US009928341B2

(12) United States Patent
Angelides

(10) Patent No.: US 9,928,341 B2
(45) Date of Patent: Mar. 27, 2018

(54) SYSTEMS AND METHODS FOR PROVIDING COMPREHENSIVE CARE FOR STOMA PATIENTS

(71) Applicant: Vivante Health, Inc., Houston, TX (US)

(72) Inventor: Kimon Angelides, Houston, TX (US)

(73) Assignee: Vivante Health, Inc., Houston, TX (US)

( * ) Notice: Subject to any disclaimer, the term of this patent is extended or adjusted under 35 U.S.C. 154(b) by 0 days.

(21) Appl. No.: 15/345,932

(22) Filed: Nov. 8, 2016

(65) Prior Publication Data

US 2017/0140103 A1    May 18, 2017

Related U.S. Application Data

(60) Provisional application No. 62/254,475, filed on Nov. 12, 2015.

(51) Int. Cl.
*A61F 5/44*       (2006.01)
*G06F 19/00*   (2018.01)

(52) U.S. Cl.
CPC .......... *G06F 19/322* (2013.01); *A61F 5/4404* (2013.01); *G06F 19/3418* (2013.01)

(58) Field of Classification Search
CPC combination set(s) only.
See application file for complete search history.

(56) References Cited

U.S. PATENT DOCUMENTS

| 6,171,289 B1* | 1/2001 | Millot ..................... A61F 5/443 604/336 |
| 7,670,289 B1* | 3/2010 | McCall ............... A61M 1/3653 210/645 |
| 8,740,865 B2* | 6/2014 | Krystek .................. A61F 5/445 340/605 |
| 2003/0009131 A1* | 1/2003 | Van Antwerp .... A61M 5/16836 604/111 |
| 2010/0030167 A1* | 2/2010 | Thirstrup ................ A61F 5/445 604/318 |
| 2011/0212090 A1* | 9/2011 | Pedersen ............ A61K 39/0011 424/133.1 |
| 2013/0324952 A1* | 12/2013 | Krystek .................. A61F 5/445 604/318 |
| 2017/0140103 A1* | 5/2017 | Angelides ............. G06F 19/322 |

* cited by examiner

*Primary Examiner* — Todd J Scherbel
*Assistant Examiner* — Guy K Townsend
(74) *Attorney, Agent, or Firm* — Elizabeth R. Hall

(57) ABSTRACT

Embodiments of the invention include systems and methods for providing comprehensive care for stoma patients. According to one embodiment, a system for providing comprehensive care for a stoma patient includes: a sensor device for detecting a fill level of an ostomy bag fitted over and around a stoma, wherein the sensor device is configured to sense one or more parameters of an effluent received in the bag; communicating the measurements to a stoma care management software application for formatting and visualization on a patient mobile device; and transferring the formatted data to an interactive wireless stoma care management platform, wherein the platform is configured to maintain a patient related database and to periodically advise the patient of needed actions as well as to provide reminders, advice and coaching.

18 Claims, 18 Drawing Sheets

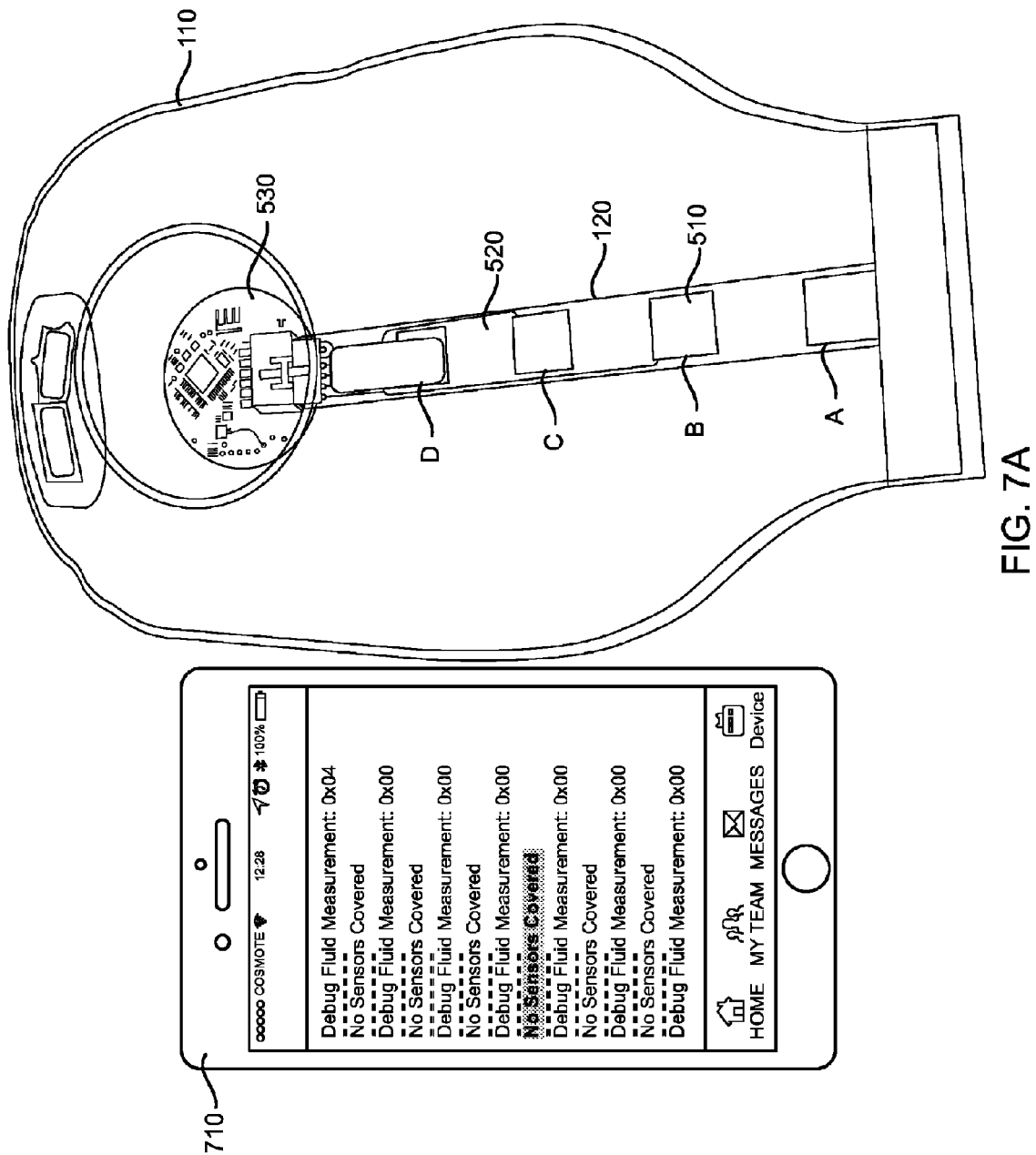

FIG. 8

| Schedule | Selected Member Profile | SESSION |
|---|---|---|

Session in queue: 2

Next in Line:

🧑 Liza Smith

Last session: 07/20/2016, 13:42
Quick overview: A quick overview of the notes the sherpa took during the last session

| Member | Scheduled | Age | Disease | Last session |
|---|---|---|---|---|
| ◉ 🧑 Liza Smith | NOW | 32 | Ostomy | 7 days ago |
| ○ 🧑 Peter Frege | Starts in 30' | 27 | Crohns | 30 days ago |

[Profile] [Start] [Postpone] [Cancel]

FIG. 10

SYSTEMS AND METHODS FOR PROVIDING COMPREHENSIVE CARE FOR STOMA PATIENTS

CROSS-REFERENCE TO RELATED APPLICATION

The present application, pursuant to 35 U.S.C. 111(b), claims the benefit of the earlier filing date of provisional application Ser. No. 62/254,475 filed Nov. 12, 2015 and entitled "Systems and Methods for Providing Comprehensive Care for Stoma Patients."

BACKGROUND OF THE INVENTION

Field of the Invention

This invention is related to systems and methods for providing comprehensive care for stoma patients. More particularly, the invention is related to a system for providing a sensor device for detecting a fill level of a stoma bag fitted over and around a stoma and a wireless platform in communication with the sensor device to periodically advise the patient of needed actions.

Description of the Related Art

An ostomy is a surgical procedure used to create a small opening or stoma on the abdominal wall for releasing waste matter from the bowel or bladder. A stoma appears like a small spout. Waste matter that comes out of the stoma is collected in an external ostomy or stoma bag or pouch.

In a colostomy procedure, the stoma is formed by drawing the healthy end of the large intestine or colon through an incision in the anterior abdominal wall and suturing it into place. The portion of the colon that is cut and extended through the abdominal wall can be in a number of locations, such as the ascending, the transverse or the descending portion. If in the descending portion, the effluent would be more dense and would be more similar to that of a person who has not had any such procedure. The further up the intestine, the less absorption would take place, and the effluent would become more unfamiliar in appearance and consistency.

In an ileostomy, an opening is made in the belly (abdominal wall) and the end of the ileum (the lowest part of the small intestine) is brought through this opening to form a stoma, usually on the lower right side of the abdomen. In either case, a collection bag is attached to the stoma. Since the collection bag is flexible and the extruding section tissue that one attaches to the collection bag is also flexible, there can be leaks at the attachment region, particularly as the bag becomes fuller and there is more fluid pressure from the bag contents at the attachment region.

In some cases, for colostomy, ileostomy or urostomy patients, the stoma may be temporary allowing the bowel or bladder to heal before the stoma is reversed. The length of time before reversal varies but most are not reversed before three months. In other cases, the stoma may be permanent.

Patients with an ileostomy or colostomy have an impaired quality of life related to the difficulties involved with having the external stoma bag and the fact that patients with a stoma have no control over their release of waste matter. Although patients with an ileostomy may have a better quality of life as compared to patients with a colostomy, both procedures limit the range of activities that recipients are comfortable undertaking. The more liquid nature of the ileostomy or urostomy effluent, which creates more fluid pressure at a stoma bag attachment region, can predispose these patients' to dehydration and their bags to overfill; whereas colostomy patients, having a higher effluent consistency, are more susceptible to blockages of the attachment region (which is narrower than the bag itself).

These problems are particularly important to patient populations with long term or permanent colostomy or ileostomy. Overfilling and breakage/leakage of the collection bag can affect a patient's ability to function in social environments, go out in public, have intimate relationships with significant others, and can interfere with sleep patterns due to high internal output and nighttime overfilling of the bag.

One difference in patients with an ileostomy bag is that because the contents are more liquefied than in a colostomy, the bag can often be drained several times before it is replaced whereas a colostomy bag must be replaced every time it is filled.

There is a need for a convenient device that can prevent unexpected bag overfilling, breakage, and nighttime accidents. The device should be capable of being configured to store and email output data to the patient's health care providers. The device should have the potential to reduce ostomy related dehydration through more accurate volume recording and sharing. The device should be configured to easily determine the rate of fill of the bag since this may predict whether a patient is headed toward dehydration.

SUMMARY OF THE INVENTION

Embodiments of the invention include a care management system for providing comprehensive care for stoma patients. The system includes: A) a sensor or sensing device associated with a measurement communicator and a data processor; B) a software application 210 for receiving, storing, and processing the measurement data communicated from the sensor device; and C) a wireless stoma care management platform residing on a computer that maintains a patient related database, correlates the measurement data with information on external data sources and patient responses to queries in order to develop a health metric for the stoma patient, and periodically advises the patient of needed actions as well as to provide reminders, advice and coaching.

One embodiment of the invention is an ostomy bag having: a) an attachment site to a patient stoma; b) at least one parameter sensor attached to the ostomy bag, wherein the parameter sensor is configured to measure one parameter of a stoma effluent received in the ostomy bag; and c) at least one measurement communicator attached to the ostomy bag, wherein one measurement communicator is configured to receive a measurement data point from the parameter sensor and to communicate the measurement data point to a stoma care management application.

Another embodiment of the present invention is a system for assisting a stoma patient with management of an ostomy bag including: a) a sensor device configured to sense one or more parameters of a stoma effluent received in the ostomy bag; b) a stoma care management application for receiving, storing and processing measurement data communicated from the sensor device, wherein the stoma care management application is configured to run on a patient mobile device; and c) a wireless platform in communication with the mobile device, wherein the platform comprises one or more portals, and wherein the platform is configured to maintain a patient related database and a programmed knowledge module for analyzing information from the database and one or more external databases.

According to another embodiment, an interactive stoma care management platform is provided. The platform includes a memory; and a processor that executes computer-executable components stored in the memory to implement the platform The computer-executable components include: (i) a knowledge module configured to analyze sensor measurement data received from a stoma care management software application, wherein the stoma care management software application is configured to run on a mobile device; and (ii) a portal configured to add contextual metadata to at least a subset of the analyzed sensor measurement data. The contextual metadata comprises one or more tags that identify an origin of the subset of analyzed sensor measurement data within one or more sub-portals. At least one sub-portal is configured to communicate an intervention trigger to a mobile device in dependence on the analyzed sensor measurement data exceeding a predefined threshold level.

In another embodiment, a stoma care management software application is provided. The application may be stored on non-transitory computer-readable medium. The medium includes computer-executable instructions that, in response to execution, cause a computing system to perform operations for stoma care management. The operations include: interfacing with a sensor device; and receiving, from the sensor device, a plurality of sensor measurement data relating to one or more parameters associated with an ostomy bag for a stoma patient.

In yet another embodiment, a method for stoma care management involves: measuring at least one parameter of a stoma effluent received in an ostomy bag; communicating data on the measured parameter to a stoma care management software application; converting the data on the measured parameter into a usable format; and communicating the formatted data to an interactive stoma care management platform for analysis and storage.

The foregoing has outlined rather broadly several aspects of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed might be readily utilized as a basis for modifying or redesigning the structures and systems for carrying out the same purposes as the invention. It should be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIGS. 7A and 7B are schematic illustrations of a mobile application configured to detect a fluid measurement in an ostomy bag according to an embodiment.

FIG. 8 is an exemplary display screen of a user sub-portal of an interactive platform according to an embodiment.

FIG. 10 is an exemplary display screen of a healthcare counselor sub-portal of an interactive platform according to an embodiment.

DESCRIPTION OF THE PREFERRED EMBODIMENTS

It is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in any appropriately detailed structure.

Figure 1:
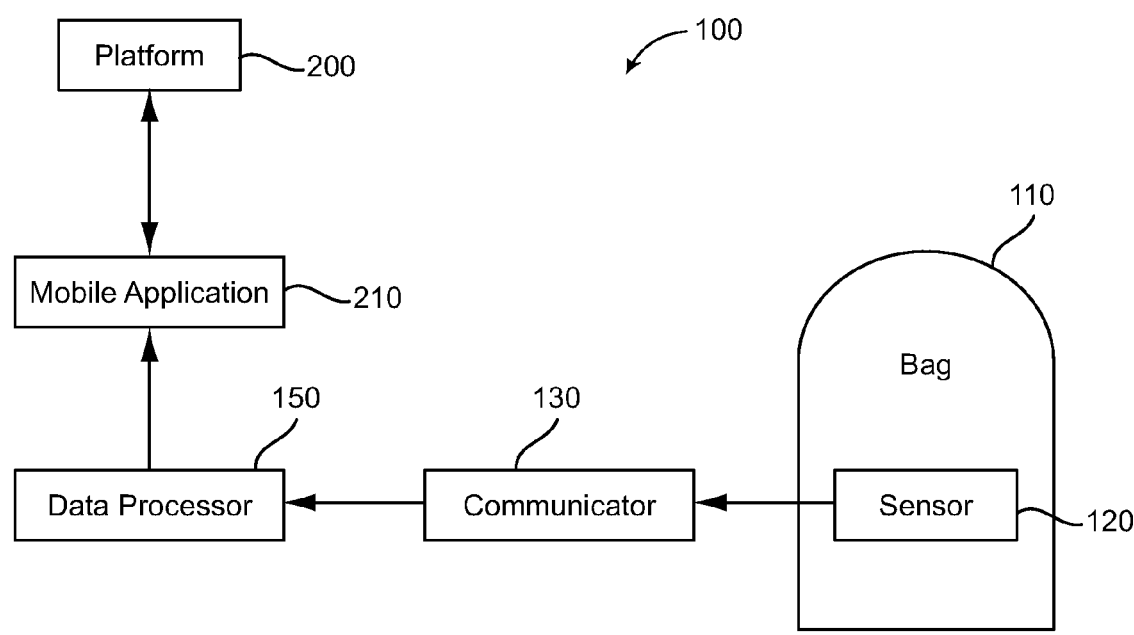
FIG. 1 is an illustration of a system for providing comprehensive care for stoma patients according to an embodiment.
Figure 2:
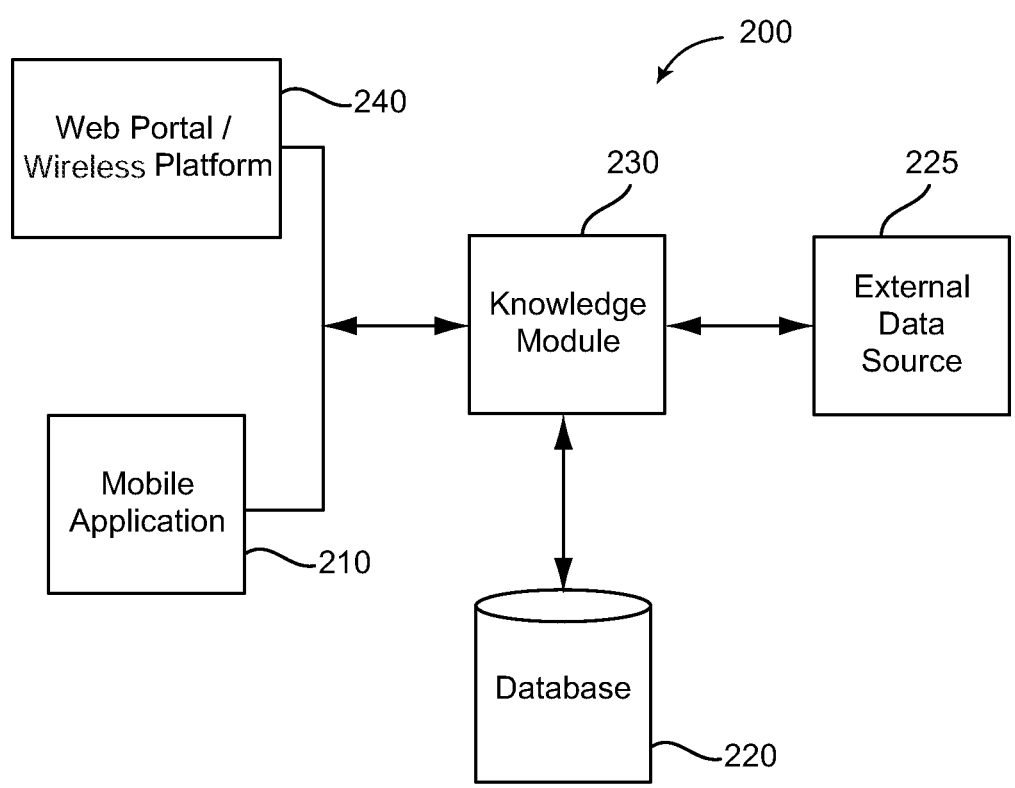
FIG. 2 is a schematic illustration of a mobile application and an interactive platform for providing care for stoma patients according to an embodiment.

Referring now to the drawings, and initially to FIGS. 1 and 2, it is pointed out that like reference characters designate like or similar parts throughout the drawings. The Figures, or drawings, are not intended to be to scale. For example, purely for the sake of greater clarity in the drawings, component size and spacing are not dimensioned as they actually exist in the assembled embodiment.

Care Management System for Stoma Patients

Embodiments of the invention include systems and methods for providing comprehensive care for stoma patients. According to one embodiment, a system for providing comprehensive care for a stoma patient includes: a sensor device for detecting a fill level of an ostomy bag fitted over and around a stoma, wherein the sensor device is configured to sense one or more parameters of an effluent received in the bag; communicating the measurements to a stoma care management software application for formatting and visualization on a patient mobile device; and transferring the formatted data to an interactive wireless stoma care management platform, wherein the platform is configured to maintain a patient related database and to periodically advise the patient of needed actions as well as to provide reminders, advice and coaching.

FIG. 1 shows an embodiment of a care management system 100 for providing comprehensive care for stoma patients. The system 100 includes: A) a sensor or sensing device 120 associated with a measurement communicator 130 and a data processor 150; B) a software application 210 for receiving, storing, and processing the measurement data communicated from the sensor device 120; and C) a wireless stoma care management platform 200 residing on a computer that maintains a patient related database, correlates the measurement data, information on external data sources and patient responses to queries in order to develop a health metric for the stoma patient, and periodically advises the patient of needed actions as well as to provide reminders, advice and coaching.

Ostomy Pouch and Sensing Device

Ostomy Pouch.

An ostomy is a surgical procedure used to create a small opening or stoma on the abdominal wall for releasing waste matter from the bowel or bladder. A stoma appears like a small spout. Waste matter that comes out of the stoma is collected in an external ostomy or stoma bag or pouch 110. An ostomy bag, stoma or collection bag, allows the stoma to drain into a sealed collection bag while protecting the surrounding skin from contamination.

Figure 4A:
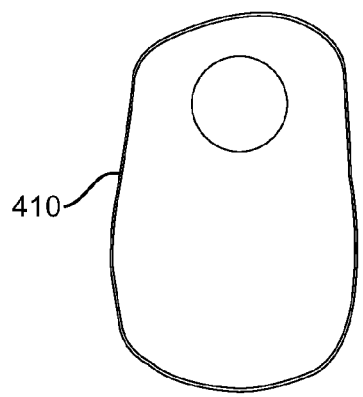
FIG. 4A is an illustration of a closed ended ostomy bag.
Figure 4B:
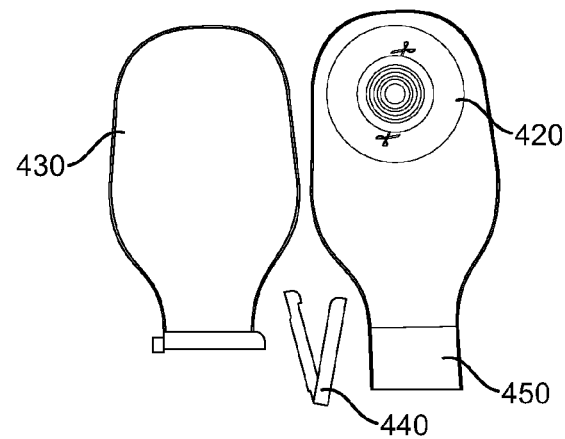
FIG. 4B illustrates an open ended ostomy bag both when it is clipped closed and when it is opened.
Figure 4C:
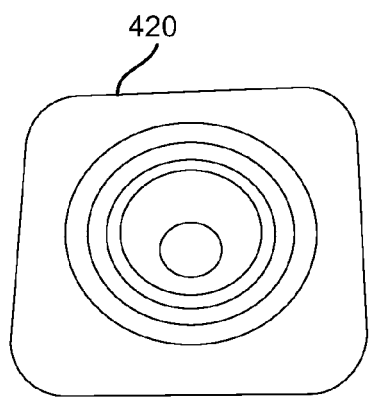
FIG. 4C is an illustration of an ostomy bag mounting plate or flange.
Figure 4D:
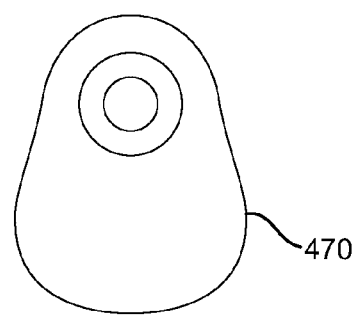
FIG. 4D is an illustration of a temporary closed ended ostomy bag.

The ostomy bag is typically a water-tight flexible elastomeric bag that is either a one-piece apparatus (illustrated in FIGS. 4A and 4D) that attaches directly to the stoma or is a two-piece apparatus (shown in FIG. 4B) that has a mounting plate 420 (such as shown in FIG. 4C), commonly called a flange, wafer or baseplate as well the bag. The flange ring 420, shown in FIG. 4C, is attached mechanically or with an adhesive to the bag. The two-piece apparatus allows the bag to be exchanged without removing the flange, as for example temporarily switching to a "mini-pouch" (shown in FIG. 4D) for swimming or other short-term activities.

Ostomy bags come as both open-ended bags 430 or closed-ended bags 410. The open-ended bags 430 have a resealable end 450 that is sealed with a closure 440. The open-ended bags can be opened to drain the contents of the bag into a toilet. The open-end 450 of the open-ended bag is generally rolled over and sealed with a Velcro-type closure or a simple clip 440. The collection bag is attached to the stoma. Since the collection bag is flexible and the extruding section of tissue that one attaches to the collection bag is also flexible, there can be leaks at the attachment region, particularly as the bag becomes fuller and there is more fluid pressure from the bag contents at the attachment region.

Sensing Device.

Referring back to FIG. 1, embodiments of the present invention have one or more sensor devices 120 attached to the collection bag. Depending on the type of sensor device 120 and its attachment to the collection bag 110, the sensor device will differ in size, shape and function. The device 120 is generally manufactured from a suitable material, such as a plastic that is resistant to hospital disinfectant cleaners.

Figure 5A:
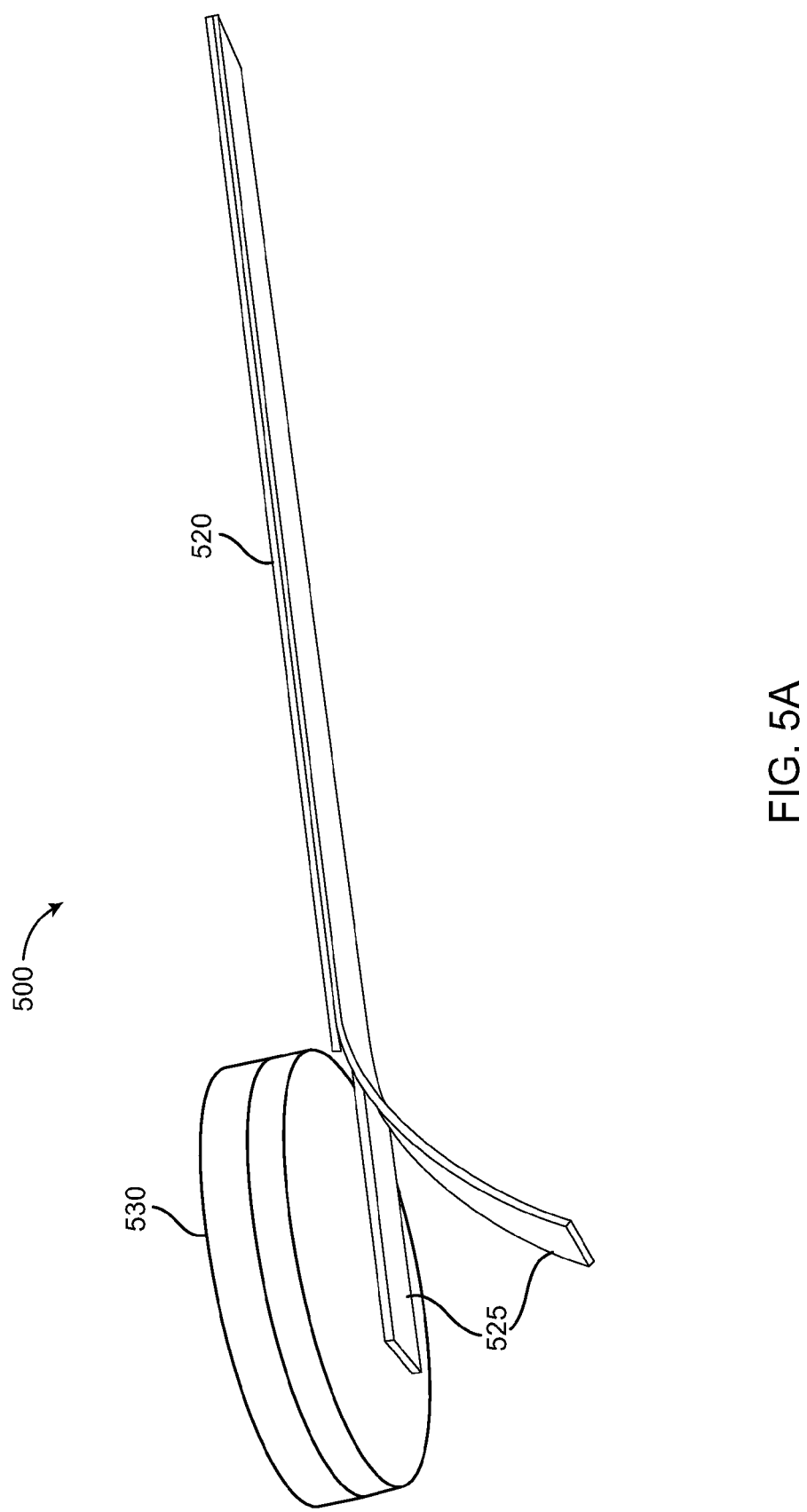
FIG. 5A illustrates one embodiment of a sensor device.
Figure 5B:
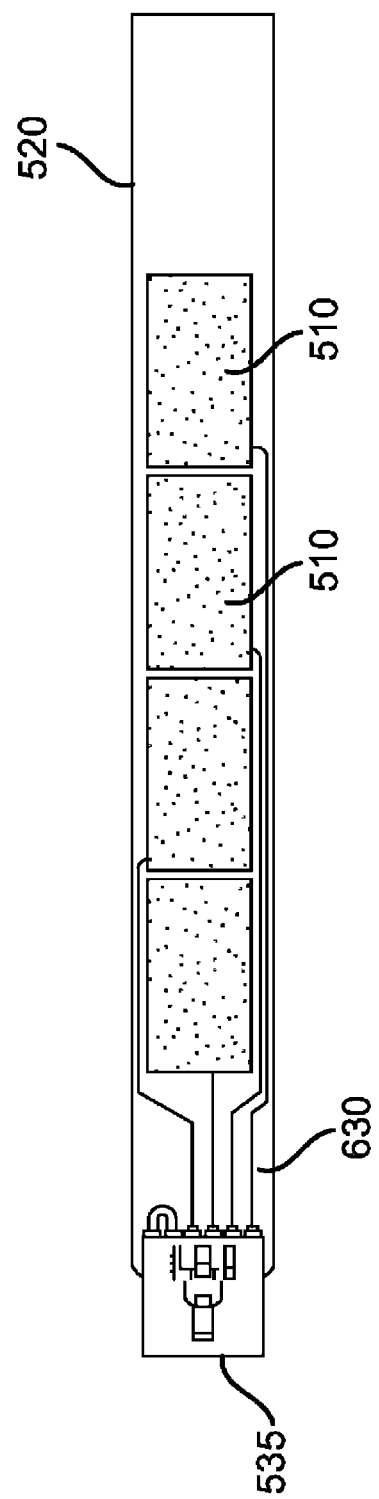
FIG. 5B is one embodiment of the mounting device with multiple parameter devices.

One embodiment of a sensor device 120 is illustrated in FIG. 5A. The sensor device 120 includes several parameter sensors 510, such as illustrated in FIG. 5B, and a measurement communicator 530 that stores and transmits each measurement of the parameter being measured by the parameter sensor 510. The parameter sensors 510 are in communication with one or more measurement communicators 530. Thus, a collection bag can be customized by a patient, a health care provider or a researcher to measure, store, calculate, communicate, record and/or track one or more desired parameters.

Figure 6A:
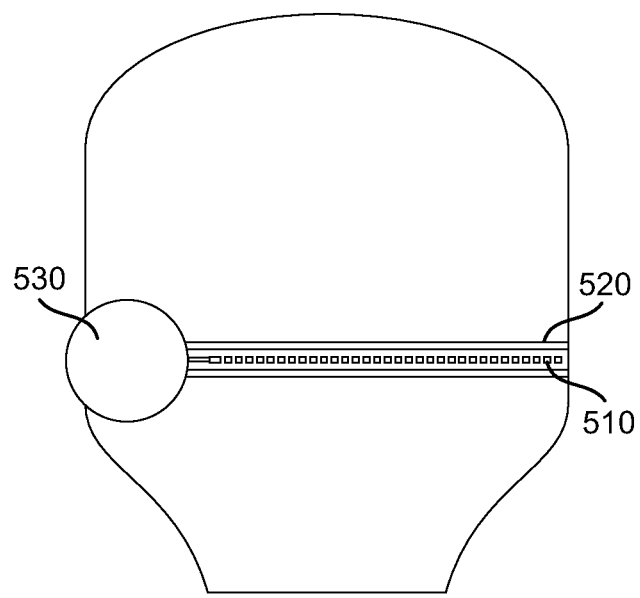
FIG. 6A is an illustration of the sensor device shown in FIG. 5A mounted on an ostomy bag.

The parameter sensor(s) 510 are typically attached to or embedded within the collection bag 110 or the flange 420. For example, FIG. 6A illustrates one embodiment of the sensor device shown in FIG. 5A having a mounting device 520 that is removably attached to the outside of an ostomy bag via Velcro type attachment strips 525, a covering with an adhesive side having parameter sensors (a Band-Aid type of attachment with one or more parameter sensors substituted for the gauze patch), or insertion into a pouch on the outside of the bag. The sensor device can be attached horizontally across one section of the bag as shown in FIG. 6A, or it can be attached vertically or diagonally to the bag. The parameter sensors 510 may be mounted in any desired position for monitoring as long as the parameter sensors are in communication with the measurement communicator 530.

Figure 6B:
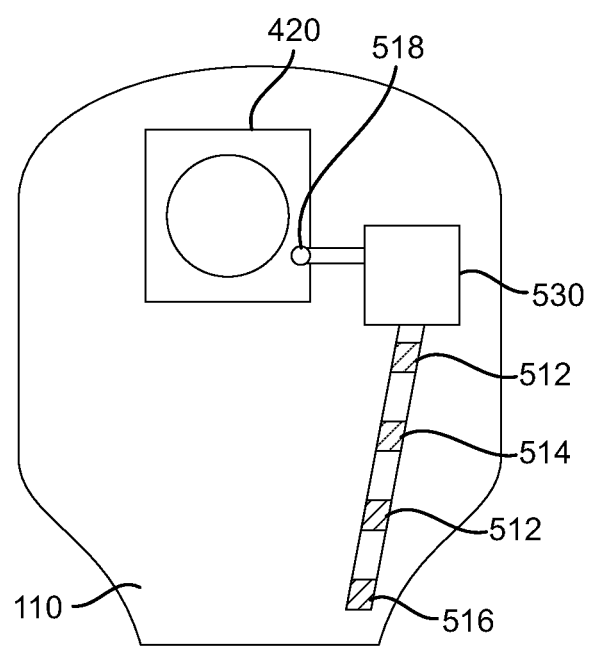
FIG. 6B is schematic illustration of an embodiment of a sensor device mounted on an ostomy bag.

The mounting device 520 may have an array of multiple parameter sensors 510 as illustrated in FIG. 5B and those parameter sensors may be the same type of sensor or they may be different sensors. For example, the embodiment of the sensor device illustrated in FIG. 6B illustrates a sensor device having multiple types of parameter sensors 512, 514, 516 and 518. Although a variety of parameter sensors can be used at various locations, it is important that each parameter sensor 510 is in constant communication with a measurement communicator 530 via a communication conduit 630, such as an optical fiber or a wire or any other communication transport conduit.

Often, the sensor device is removably attached to the outside of the ostomy bag 110 so that it can be removed and placed on another bag. Alternatively, parameter sensors 510 may be embedded within the bag and disposed with the bag. If the parameter sensors 510 are embedded in the bag, then the measurement communicator 530 will typically be removably attached to the outside of the bag at a site having communication with each of the embedded parameter sensors 510. In such cases, the measurement communicator 530 is attached mechanically or with an adhesive to the communicator attachment site 620 on the ostomy bag 110.

Figure 6C:
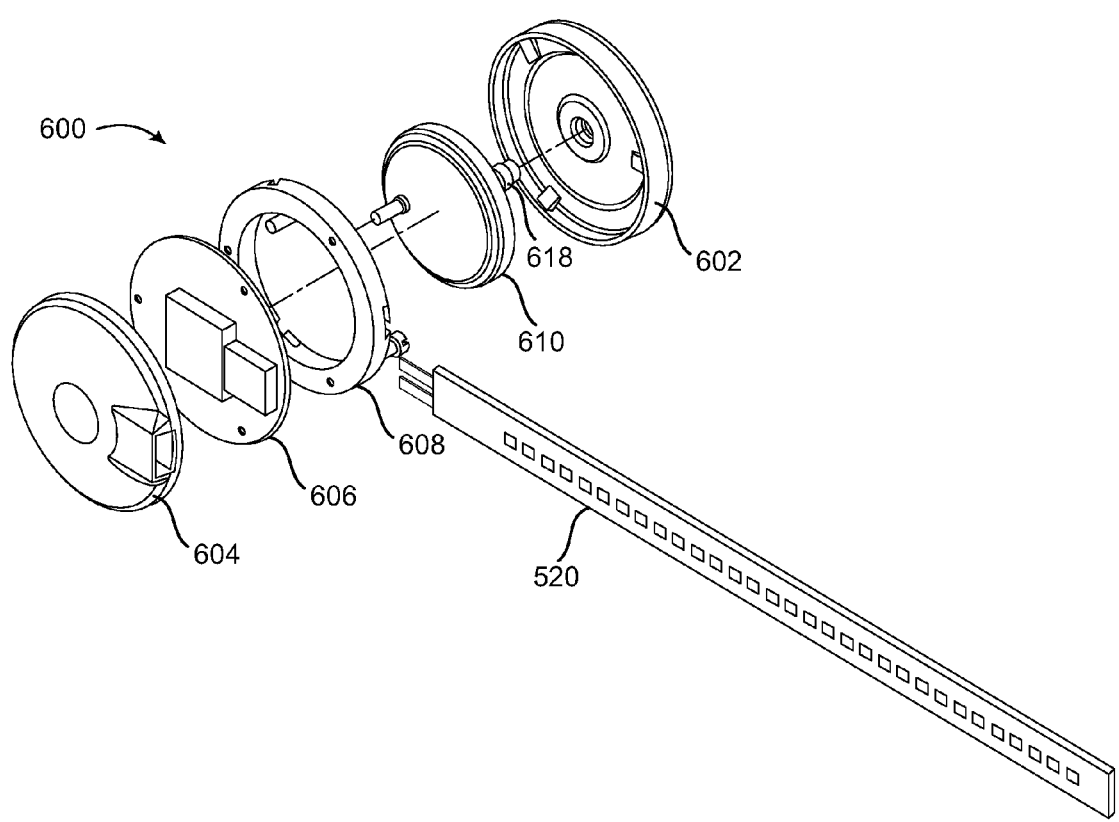
FIG. 6C is an exploded view of one embodiment of a sensor device.
Figure 6D:
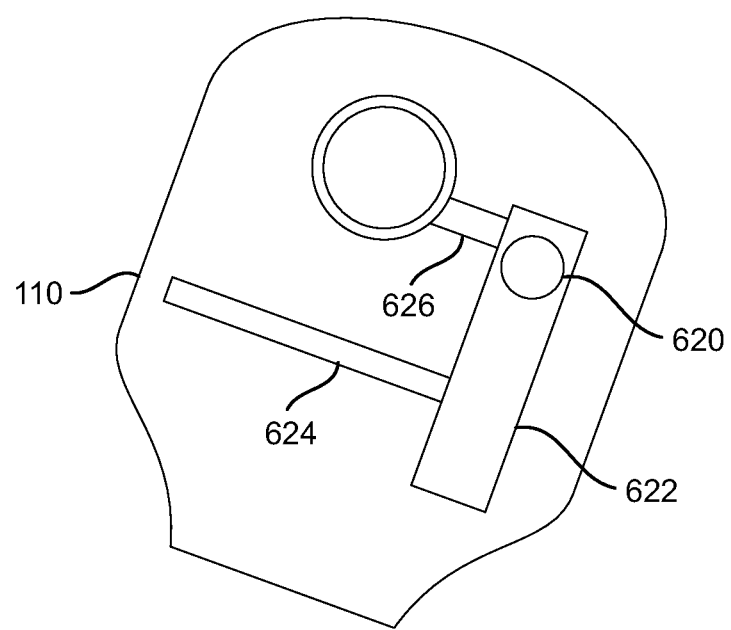
FIG. 6D is a schematic side view of a collection bag with embedded parameter sensors.

One embodiment of an ostomy bag 110 with embedded parameter sensors, shown in FIG. 6D, has at least one outside elastomeric layer 622 sealed to a section of the bag with at least one parameter sensor sandwiched between the outside layer and the bag. Since there may be a number of parameter sensors, of one or more type, embedded between the outside layer and the bag; there may be one or more outside layers 622, 624, 626 that are attached to the outside of the bag. These outside layers may be different sizes and shapes and will be positioned at different locations on the bag.

The outside layers may be open at one end to serve as a pocket or a pouch for the sensor device 120, or they may be sealed to the outside of the bag along sections of their perimeter. The outside layers are designed to protect the parameter sensors 510 and their communication conduits 630, such as an optical fiber or a wire shown in FIG. 6E, from either physical or chemical damage during bag use to ensure the communication link between the parameter sensor 510 and its connection to the measurement communicator 530 at the communicator attachment site 620. Embedded parameter sensors may be particularly useful for patients that empty their bag and reuse it multiple times.

Types of Sensors.

Although the description continues with references to "a" (single) sensor device, it should be understood that different sensor devices and different parameter sensors may be employed to provide and communicate different sensed parameters. A non-exhaustive list of different example types of parameter sensors 510 may be employed for measuring the following:

Volume:

a) Flex/bend and stretch sensors contained within an adhesive strip can detect changes in resistance, as the flex and stretch sensors bend or are extended the electrical resistance changes and is recorded by the measurement communicator; b) Pressure sensors can measure the pressure exerted by the filling bag and thus with the known volume of the bag, this measurement is reported as the volume of bag content; and c) Level measuring sensors can be placed at defined vertical locations on the bag such that capacitance sensors, ultrasonic sensors or a microwave propagation phase shift sensors can measure the liquid and solid level of the bag as it fills.

Turbidity:

a) IT optical backscattering sensors having an embedded small IR LED in the parameter sensor with photodiodes surrounding the IR LED to measure the backscattering of the IR light from the particles in the bag with which the IR light interacts. Such measurements can provide the size of the particles and report on the turbidity (and thus consistency) of the contents; and b) Ultrasonic sensors (such as Doppler sensors) can be used as an alternative to the IR optical backscattering, the ultrasonic sensors can also be used to measure the contents and consistency of the stoma effluent in the bag.

Odor-Olfaction:

Nanosensor (or "e-nose") circuits can be used to measure a variety of odors, for example a methane and ammonia sensor can report any odors or leakages within the immediate environment of the parameter sensor.

Temperature:

A differential temperature sensor can be used to record changes in the temperature of the bag and/or the stoma effluent or bag contents.

Liquid Flow:

A flow sensor can be placed at the top of the bag and/or at the opening of the bag proximal its attachment to the stoma to measure all stoma effluent flow into the bag.

Leakage:

A parameter sensor that uses ink jet electrodes printed on paper can be used to measure leakage. The sensor paper is placed at the site of bag attachment to the stoma with the sensor paper surrounding the stoma or attached to the flange 420. As the paper gets wet, from leakage, the electrodes changes resistance and report this to the communicator 530.

Activity:

A tri-axis or multi-axis accelerometer chip may be embedded on a circuit board within the measurement communicator 130 of the sensor device to report on movement and activity. The measurement communicator is configured to receive data from the accelerometer chip. Using the data, the direction/orientation of the patient's body can be calculated. This facilitates the determination of whether the patient is walking, lying down, sitting up with his body in an upright position, or leaning forward or any other direction. This information can be used to evaluate the fluid level measurements.

In one embodiment, the parameter sensor 510 is a soft, ultrasensitive wireless stretch sensor. In another embodiment, the parameter sensor 510 may be a capacitive sensor. Capacitive sensors may be used to detect and measure fluid levels in the collection bag 110. In yet another embodiment, such as shown in FIG. 6B, one parameter sensor 518 may be for detecting leakage, one parameter sensor 512 may be for turbidity, one parameter sensor 514 may be for temperature, and one parameter sensor 516 may be to report specific movements.

In one embodiment, as the bag 110 fills up, the parameter sensor 510 can measure, through the resistance of the strip, the bending and stretching of the bag. In another embodiment, the parameter sensor 510 is clipped to the edges of the bag 110 to sense the bending and stretching and conformational changes of the bag 110 as it fills up.

In yet another embodiment, the parameter sensor 510 is a capacitive fluid sensor. Capacitive fluid sensors can measure the change in capacitance as the fluid levels rise. This embodiment can include two electrodes in a circuit or an array of sensors running vertically up and down the bag to measure increasing volume levels. The capacitance between the two electrodes is different when there is air (a non conducting medium of low dipole), versus water (having a higher dielectric constant). Therefore, as measurements are taken at predetermined set time intervals the fluid levels rises and the bag fills up. In this case the fluid would have slightly different dielectric properties than water since it is urine and waste and there will be a detectable change along the many electrodes that would measure specifically where the fluid is in the bag.

Measurement Communicator.

Every parameter sensor 510 must communicate the data gathered by the parameter sensor to a measurement communicator 530 where it is gathered, identified with a particular parameter sensor device 510 and typically processed before being further communicated to the platform 200. The sensor device 120 includes at least one parameter sensor 510, at least one data processor 150, and at least one measurement communicator 530 that stores and transmits each measurement of the parameter being measured by the parameter sensor 510.

Figure 6E:
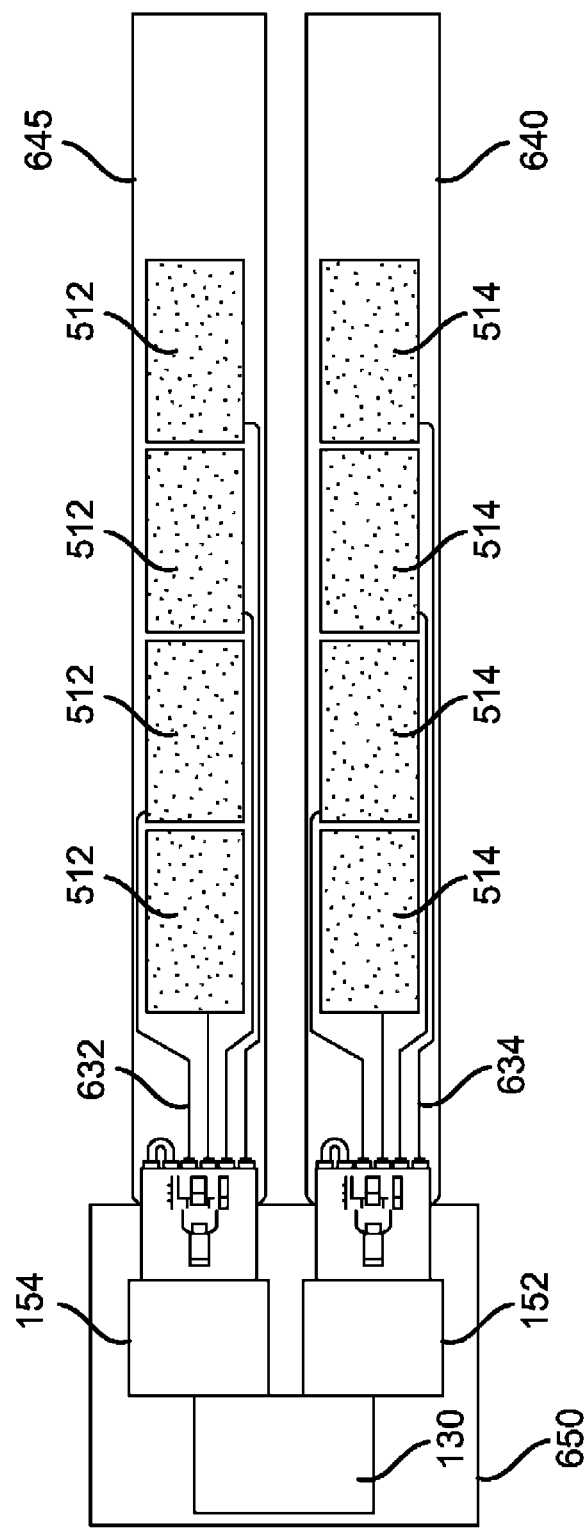
FIG. 6E a sensor device with two parameter sensor arrays connected to data processors and a measurement communicator.

In one embodiment a single parameter sensor 510 is in communication with a single measurement communicator 530. In other embodiments, multiple parameter sensors are in communication with a single measurement communicator. For example, one embodiment shown in FIG. 6E has two parallel arrays 640 and 645 where each array has multiple parameter sensors of a single type. Sensor array 640 has several parameter sensors 514, whereas sensor array 645 has several parameter sensors 512. Each sensor in each array must communicate with a data processor and a measurement communicator 130. The embodiment shown in FIG. 6E shows that each sensor 514 in the sensor array 640 communicates with a data processor 152 through a communication conduit 634, while each sensor 512 in the sensor array 645 communicates with a data processor 154 through a communication conduit 632. The data processors 152 and 154 may be the same or different and the communication conduits 632 and 634 may be the same or different. For example, the communication conduits 632 and 634 may be wire connections or communication conduit 632 may be wire connections and communication conduit 634 may be optical fibers. In another embodiment (not shown), the sensors may wirelessly communicate with the data processors.

FIG. 6C is an exploded view of one embodiment a sensor device 600. The measurement communicator 530 has an upper 602 and a lower 604 end cap that are fitted together to enclose a data processor having a control board 606 such as a PCU (Programmable Control Unit) or a PCB (Printed Circuit Board), a battery retainer 608, and a battery 610. The mounting device 520 has an array of parameter sensors 510. In addition, the sensor device 600 may optionally have a parameter sensor such as an odor sensor 618 that protrudes through the upper end cap. Each parameter sensor communicates with the data processor or control board 606 that collects, identifies and processes each measurement from each parameter sensor and the broadcasts the measurement through the measurement communicator to the mobile application 210. Typically, the data processor 150 receives the measurement signal from a parameter sensor 510, reformats the raw measurement signal and adds an identifier such as the time of the measurement and/or the identity of the specific parameter sensor that took the measurement.

The measurement communicator 530 is designed such that when the mounting device 520 is assembled with the measurement communicator that the parameter sensors mounted on the mounting device or embedded within the bag are in communication with the control board 606. Whenever an odor sensor 618, or any other sensor, is included in the sensor device, that parameter sensor must also have a communication conduit 630 aligned to allow communication between the parameter sensor and the control board.

Stoma Care Management Software Application

According to an embodiment, measurement data such as a rate of fill or fill level measurement data from the bag 110 is periodically transmitted to a stoma care management software application. FIG. 2 illustrates an interactive platform for stoma care management 200 according to an embodiment of the present disclosure. As shown in FIG. 2, the stoma care management software application or mobile application may be configured to run on any portable or mobile device 210. The stoma care management software application may be available for download through app stores or distribution platforms. The mobile device 210 may include a smart phone or a tablet computer. The stoma care management software application includes computer program instructions for receiving the measurement data from the measurement communicator 130 via the data processor 150. The measurement data is transmitted from the data processor 150 in binary format. The stoma care management software application includes computer program instructions for converting the transmitted data into a suitable format (for example, hexadecimal format). The stoma care management software application further includes computer program instructions for interpreting the formatted measurement data using a dictionary application. The stoma care management software application further includes computer program instructions to present a visual representation of the fill levels of the collection bag 110. The visual representation may be displayed on a display screen of the mobile device 210.

The measurement data is transmitted from the measurement communicator 130 to the mobile device 210 wirelessly through passive RFID, or a low energy Bluetooth radio or a GSM radio transmission, or direct transmission through the network to a server using wireless networks (a GSM or CDMA mobile system). The formatted measurement data is transmitted to a platform for stoma care management 200 where it is analyzed and intervention triggers are activated as required.

Interactive Platform for Stoma Care Management

According to another embodiment, a computerized platform 200, methods and computer-readable media are provided for stoma care management. By way of example and not limitation, the stoma care management software application running on a mobile device periodically receives measurements from the mobile application via the data processor and the measurement communicator on the fill levels of the collection bag. The measurements are interpreted by the stoma care management software application and the data is transferred to an interactive platform 200 for stoma care management. The platform includes a knowledge module 230. The knowledge module is a data repository and is further configured to analyze the data received from the stoma care management software application and transfer the results of the analysis to a server or portal 240 for stoma care management. The portal includes a user sub-portal that is configured to provide real-time information and intervention to the stoma patient.

The platform 200 can be configured to deliver personalized care solutions for a stoma patient using information from a number of devices (including the aforementioned sensor device 120 and measurement communicator 130). In one or more embodiments, the platform 200 can facilitate the interaction between a stoma patient, a caregiver, a financial/claims administrator and any other authorized user. Access to the platform 200 may be controlled by a system administrator. Only users with authorized credentials may be allowed access to the platform 200. For example, the memory may include cloud storage that stores profiles for one or more stoma patients that define at least one of access privileges or preferences for respective patients.

The platform 200 can include a multitude of interrelated elements. Embodiments of the platform 200 can be implemented to some extent as software modules installed and running on one or more processing systems ('computer'), such as servers, workstations, tablet computers, PCs, personal digital assistants ('PDAs'), smart phones, and so on. The processing systems may include at least one computer processor as well as a memory (not shown).

The processor can represent one or more general-purpose processing devices such as a microprocessor, central processing unit, or the like. More particularly, the processor may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor may also be one or more special-purpose processing devices such as an application specific integrated circuit (ASIC), a field programmable gate array (FPGA), a digital signal processor (DSP), network processor, or the like. The processor can be configured to execute instructions for performing the operations and steps discussed herein.

The computer can also include a computer readable storage medium on which is stored an appropriate operating system (not shown). A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. One or more sets of instructions (e.g., software) embodying any one or more of the methodologies or functions described herein may also be stored on the computer-readable medium. The instructions may further be transmitted or received over a network.

Instructions or program code embodied on the computer readable medium may be transmitted using any appropriate medium, including but not limited to wireless, wireline, optical fiber cable, RF, etc., or any suitable combination of the foregoing. Computer program code for carrying out operations of the present invention may be written in an object oriented programming language such as Java, Smalltalk, C++ or the like. However, the computer program code for carrying out operations of the present invention may also be written in conventional procedural programming languages, such as the "C" programming language or similar programming languages.

The memory may include both volatile random access memory ('RAM') and some form or forms of non-volatile computer memory such as a hard disk drive, an optical disk drive, or an electrically erasable programmable read-only memory space (also known as 'EEPROM' or 'Flash' memory). The memory can be connected to the processor and to other system components. The platform 200 may also include one or more input/output network interface device (not shown) for implementing user-oriented input/output through software drivers and hardware for controlling output to input/output devices such mobile devices 210 through a network. The platform 200 can be accessible to any number of other devices, user machines and users through a network. The other devices can be mobile phones, desktop computers, laptop computers, handheld computers or similar computing device. The network can be local area network (LAN), such as an intranet within a company, a wide area network (WAN), such as the Internet or similar communication system. The network can include any number of networking and computing devices including any number of wired and wireless devices. The network may include connections, such as wire, wireless communication links, or fiber optic cables.

Knowledge Module.

The platform 200 may include a knowledge module 230. The knowledge module includes a database comprising patient related data 220. The database 220 is a data repository for measurement data received from the measurement communicator 130. The database 220 can be a local storage unit or a remote storage unit. The database 220 may be a magnetic storage unit, optical storage unit, solid state storage unit or similar storage unit. The database 220 can be a monolithic device or a distributed set of devices. The database 220 can further include information on sensor identification numbers, the time period with ostomy, how frequently the stoma bag is changed and/or replaced, the volume, activity, usual consistency of the effluent/waste, problem areas with the bag, meal tags, calculated values, tips, alerts, rules, messaging, personalized meal plans, user input data relating to foods consumed and activity level and duration, etc.

The knowledge module 230 may be implemented as one or more sub-modules operating in separate software layers or in the same layer. These one or more sub-modules may be incorporated as part of the operating system, in the software stack, in hardware, in firmware (such as in the BIOS), or in any other manner as will occur to those of ordinary skill in the art. The knowledge module 230 processes information from the database 220 and one or more external data sources to determine personalized clinical and nutritional decision analytics. The external data sources can include a laboratory, insurance companies, media companies, call enters, care providers, account administrators, durable medical equipment (DME) suppliers, and other sources.

The knowledge module 230 may include one or more algorithms that provide both content and personalized rules to provide feedback to the patient in real time. For example, the knowledge module 230 may include code for predicting trends based on effluent parameters and summary snapshots (for example, average flow changes). The information and analysis may be stored in database 220. The knowledge module 230 may include instructions to implement one or more rules. For example, the rules may pertain to a daily meal or activity plan for the patient, a matching of the patient to a coach, nutrition guidance, client reports and predictions, member health profiles and video/chat sessions.

The patient's body mass index (BMI) and basal metabolic rate (BMR) are also preferably determined by the knowledge module 230. These metrics (and the type of patient ostomy) are transmitted to the database 220, which also includes the user's personalized health profile and preferences. Various parameters are considered in determining recommendations, educational messages, and directives to the patient. The knowledge module 230 then processes data measurement to determine useful patient information (e.g., estimated fill rate to send alerts of needed bag changes, etc.) and transmits related information to the user, including information relating to nutrition, exercise advice and treatment decisions.

Portal.

The platform 200 further includes a secure server or portal 240. The portal is typically web-based. The portal 240 receives analyzed data content from the knowledge module 230. The portal 240 provides one or more interfaces for reporting and displaying the data from the knowledge module 230. The portal 240 can be used to create and display profiles of individual members/patients. The portal 240 can be used to display information on a patient's clinical progress, medications, nutritional status etc. The portal 240 communicates with mobile devices so that the patient may view the desired patient related data on a mobile device. In one embodiment, the portal 240 may be accessed from the same mobile device 210 that is configured to run the stoma care management software application.

The portal 240 can be used to track patient preferences, especially those relating to diet and exercise. The tracking of favorites and the updating, analyses and recommendations based on patient favorites is normally a data-intensive function. The tracking and updating of patient favorites is generally based on information either gathered from the patient at an interview, or based on responses to queries from the patient. Accordingly, the tracking, updating, analyses and recommendations based on favorites are normally performed by the knowledge module 230, following transmission of real-time information on fill rate projections from the mobile device 210. The recommendations for eating can be highly specific and personalized (e.g., eat X calories of carbohydrates selected from "your favorites" mashed potatoes and pinto beans; Eat X calories of lean protein, selected from "your favorites" shrimp and egg whites). Similarly, recommendations for exercise can include recommendations for exercise duration and exertion level.

Furthermore, several messages can be sent based on the projected fill rate (e.g., the bag is X hours from needing a change or that the bag is full and needs immediate changing). Or, the patient can be directed to stop eating after a certain time or the patient may be directed to stop or start exercising. Once projected fill rates generate a profile for the patient—where all these factors are tracked and a projected fill rate is established, together with a warning system based on the projected volume of contents within the bag and when it is likely to be full.

The portal 240 may also track the patient's fluid intake rates and actual outflow (for example, the volume of urine collected in the bag). Using predictive algorithms, the system 200 can predict rate of fill and other calculations. These calculations may be used to target nutrition and "IN" and "OUT" fluid levels to ensure that the patient does not suffer from dehydration. Dehydration happens when a patient loses more fluid they take in. When this happens, their body doesn't have enough water and other liquids to carry out its normal functions. Dehydration is a common problem for stoma patients, particularly those who have had an ileostomy. Normally, the large intestine absorbs water back into the body as solid waste goes through. An ileostomy keeps food and liquid from entering the large intestine, so water cannot return to your body increasing the likelihood of dehydration. Patients that do not get enough liquid can end up in to the emergency room or back in the hospital. In fact, one of every five new ileostomy patients is readmitted to the hospital for dehydration. The tracking and recording of a patient's fluid intake and output by the knowledge module 230 can help the patient control their fluid balance and can be very helpful in developing patient alerts and advice from the patient's health care provider.

A number of factors can contribute to the volume/rate of fill/quality of effluent collected in the collection bag. Therefore, the portal 240 is also configured to provide personalized nutritional, lifestyle, exercise, and educational information to guide the patient such that they may have a better quality of life. The coaching may be provided by a specialized coach, or computerized program, such as a "Health Sherpa®", a medical professional, nutritionist, or a caregiver. Long term coaching may include review through the patient's healthcare provider and may involve providing a personalized plan of treatment with the information collected. Therefore, the system 200 facilitates patient-centered health care delivery and it can also empower the patient in making educated decisions.

The platform 200 and its ability to communicate with mobile devices and various computers or processors provides both short and long term benefits. The short term advantages of this platform may include real-time alerts so that there is no overfilling and/or bursting of the bag during the day or when the patient is sleeping; real-time feedback that includes dietary and nutritional information and liquid intake to help regulate every day health; reference to trends on bag volume; aid in meeting nutrition requirements and the absorption of foodstuffs; and the enablement of individual reporting and monitoring of ostomy output. The platform can also facilitate remote tracking by health care professionals by allowing hospitalized patients and nursing stations with multiple ostomy patients (such as an oncology section) to automatically alert the nursing station that a bag needs changing. The constant monitoring that tracks the output and predicted fill rates of multiple patients can help with the care and management of hospitalized patients. This can reduce the reliance on stoma care nursing staff. Furthermore, this can provide physicians with concrete evidence of bowel activity prior to discharge. Additionally, it may reduce a length of stay in the hospital for new ostomy patients with more real time data and nutritional counseling prior to discharge.

The long term advantages of the care management system 100 for stoma patients include the conservative utilization of ostomy bags based on actual fill rates rather than arbitrary scheduled changes; the reduction of skin irritation and infections by preventing leakages and bursting of a bag; the actual measurement of fluid intake and output to reduce dehydration events and reduce hospital admissions; patient empowerment by allowing patients to follow their own health care trends to optimize their nutritional intake based on actual measurement data of food volume/hr, volume/day and the tagging of food volumes at meal times.

Figure 3:
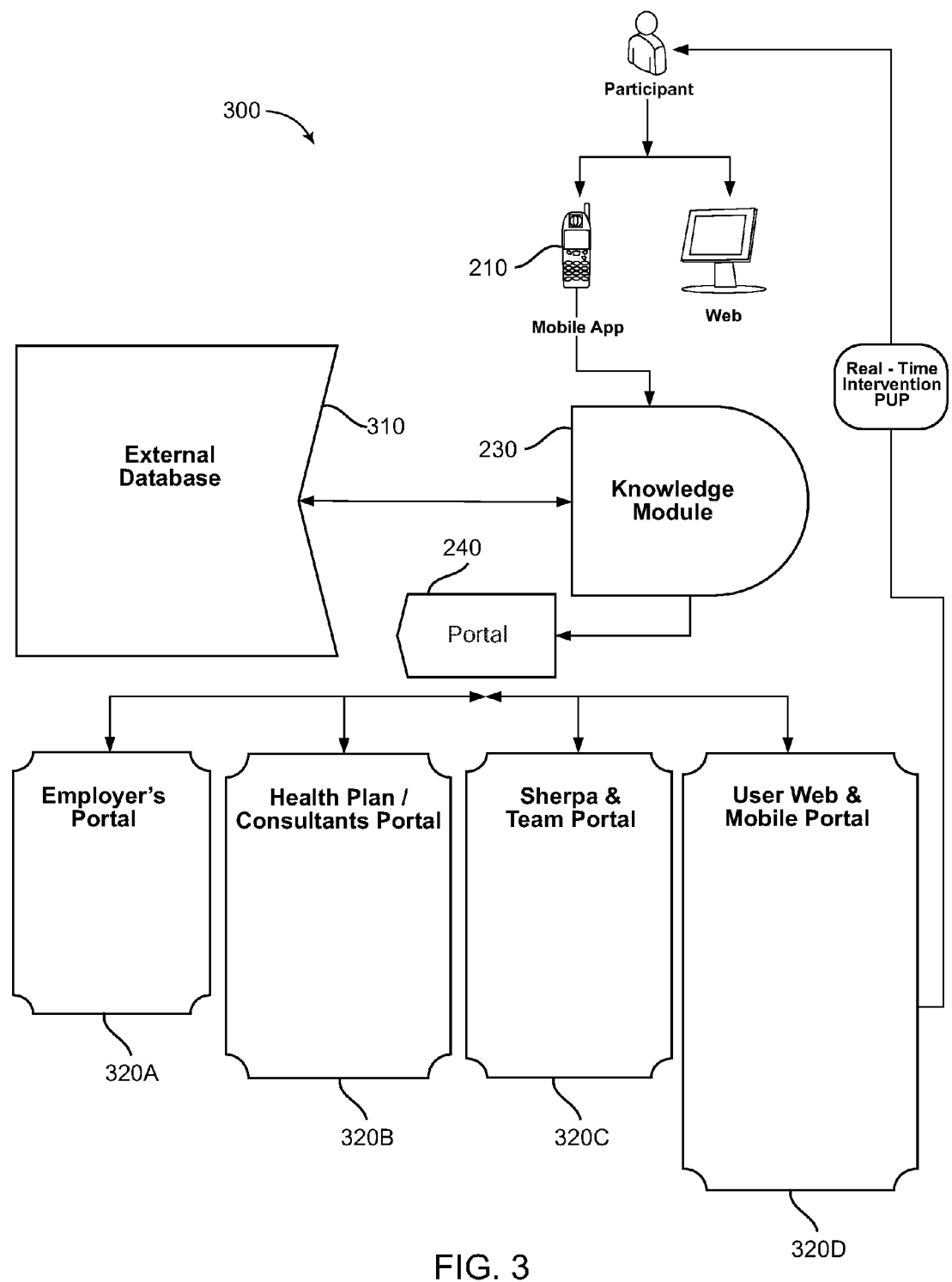
FIG. 3 is another schematic illustration of the mobile application and interactive platform for providing care for stoma patients according to an embodiment.

FIG. 3 represents an embodiment 300 of the platform for stoma care management. The fluid levels in a collection bag of a stoma patient/participant are measured on a periodic basis. The measurement data is transmitted to a stoma care management application running on a mobile device 210 for formatting and visualization. The formatted measurement data is transmitted to the platform for stoma care management.

The platform includes a knowledge module 230. The knowledge module 230 differs from a standard database since in this case further knowledge or informational data may be derived from existing knowledge using inference, analysis and continual monitoring data from the patient. Thus, the knowledge module 230 is a data repository and a "care" analysis engine. The knowledge module 230 can include a database or a data repository for the formatted measurement data. As shown, the knowledge module 230 can also receive data from and transfer data to an external database 310. The external database 310 may include data from various sources, such as laboratories, insurance companies, hospitals/clinics, media companies, 24/7 call centers/caregivers, account administrators, and other sources. The data from the external database 310 can be extracted and transferred to the knowledge module 230 using dynamic APIs. A suitable interface can be used to edit the knowledge module; for this purpose, the interface exposes a set of APIs in corresponding libraries. These APIs allow submitting commands for adding, removing, or updating of data in the knowledge module 230.

The knowledge module 230 may further include computer program instructions for analyzing the formatted measurement data from the stoma care management software application and data received from external database 310 to provide a knowledge base and healthcare advocacy information for the stoma care patient. The knowledge module 230 can also include computer program instructions to communicate the analyzed data in real-time to a secure portal 240.

The portal 240 may include a plurality of sub-portals. For example, the portal 240 may include, without limitation, an Employer's Portal 320A, a Health Plan/Consultant's Portal 320B, Health Sherpa/Caregiver Portal 320C and a User Portal 320D. The portal 240 is configured to add contextual metadata to at least a subset of the analyzed sensor measurement data. The contextual metadata can include one or more metatags that identifies an origin of the subset of analyzed sensor measurement data within the one or more sub-portals. The contextual metadata further comprises at least one of a unique identifier associated with a collection bag for the stoma patient, the patient name, a measurement time and a measurement date.

The Employer's Portal 320A may be configured to receive data from the knowledge module 230 that is relevant to an employer of a stoma patient. For example, the Employer's Portal 320A may include aggregate HIPAA information, compliance reports, performance dashboard, and other related information.

The Health Plan/Consultant's Portal 320B may be configured to receive data from the knowledge module 230 that is relevant to a health plan manager/consultant. For example, the Health Plan/Consultant's Portal 320C may include personal health records, financial administration records, performance metrics, and other related information.

The Health Sherpa/Caregiver Portal 320C may be configured to receive data from the knowledge module 230 that is relevant to a counselor/caregiver of a stoma patient. For example, the Health Sherpa/Caregiver Portal 320C may include clinical summaries, electronic medical records, prescription information, lab records, personal health records, clinical notes, clinical alerts, information on health coaching and previous coaching sessions with the patient, assessment tools, intervention tools and other related tools and data.

The User Portal 320D may be configured to receive data from the knowledge module 230 that is beneficial to a stoma patient. The User Portal 320D (and any of the other portals 320A-C) is an interactive portal and it may be accessible from the Internet or as a mobile software application. The User Portal 320D is configured to receive a plurality of information from the patient on a periodic basis. For example, the user can input how s/he feels on a daily basis. The User Portal 320D is further configured to provide information on daily diet and exercise plans, on-demand and schedule videos and chat sessions with the Health Sherpa and caregiver team, education and feedback, personalized lifestyle and behavioral resources, progress status to goals and other related information. Advantageously, the User Portal 320D is configured to provide alerts and reminder. These can be transmitted to the patient's mobile device 210 or on another computing device and may be presented via application software. Alternatively, the information may be contained in text messages, electronic mail messages or other general-purpose application software resident on the mobile/computing device. The User Portal 320D is also configured to provide real-time interventions using a personalized user profile for the patient.

Figure 8:
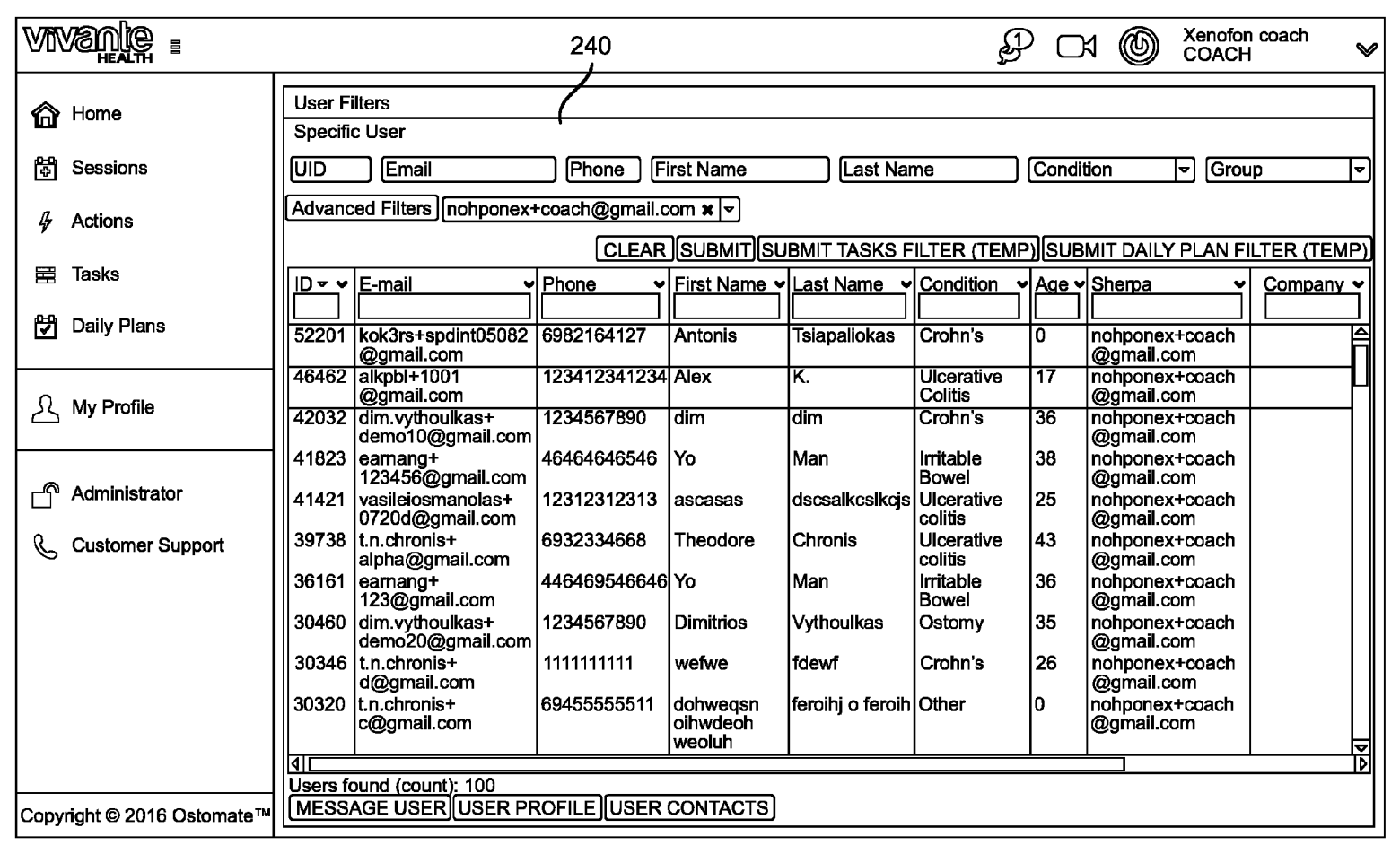

As shown in FIG. 8, information for identifying a patient, such as email, user id, phone, first and last names, medical condition, age, company name are entered in the user portal 240. A "Health Sherpa®" may be matched with each patient. Information on the Sherpa may also be entered in the portal 240. Additional information such as the patient's weight, height, daily diet and exercise plans, daily tasks, daily or weekly health status, stress levels, etc. may also be entered in the knowledge module. The portal 240 can be configured to allow the user (for example, the Sherpa) to message the user, retrieve the user profile and contacts, etc. The portal 240 may use an email authentication method, for patient authentication. Other authentication methods, such as authentication of the mobile device, are also applicable.

Figure 9:
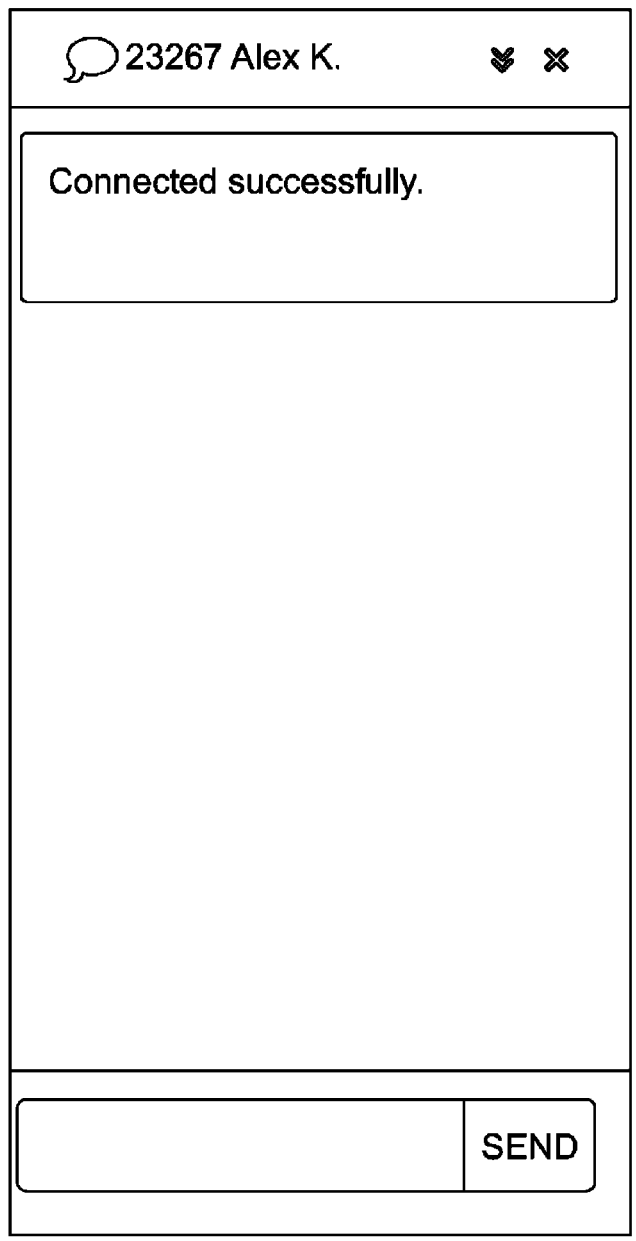
FIG. 9 is an exemplary chat screen for a healthcare counselor to connect with a stoma patient according to an embodiment.

The portal 240 can be configured to facilitate a real-time messaging or chat session between the patient and the Health Sherpa®. An exemplary display is shown in FIG. 9. Also, as shown in FIG. 10, the portal 240 is configured to allow the user to determine the number of sessions in queue and to access predetermined information on previous coaching sessions with the patient.

A high-security firewall (not shown) is used to provide a secure communication channel between the knowledge module 230 and the portals 240 and mobile application 210. The users/patients are required to authenticate themselves via an authentication layer.

Effluent Measurement

Figure 7B:
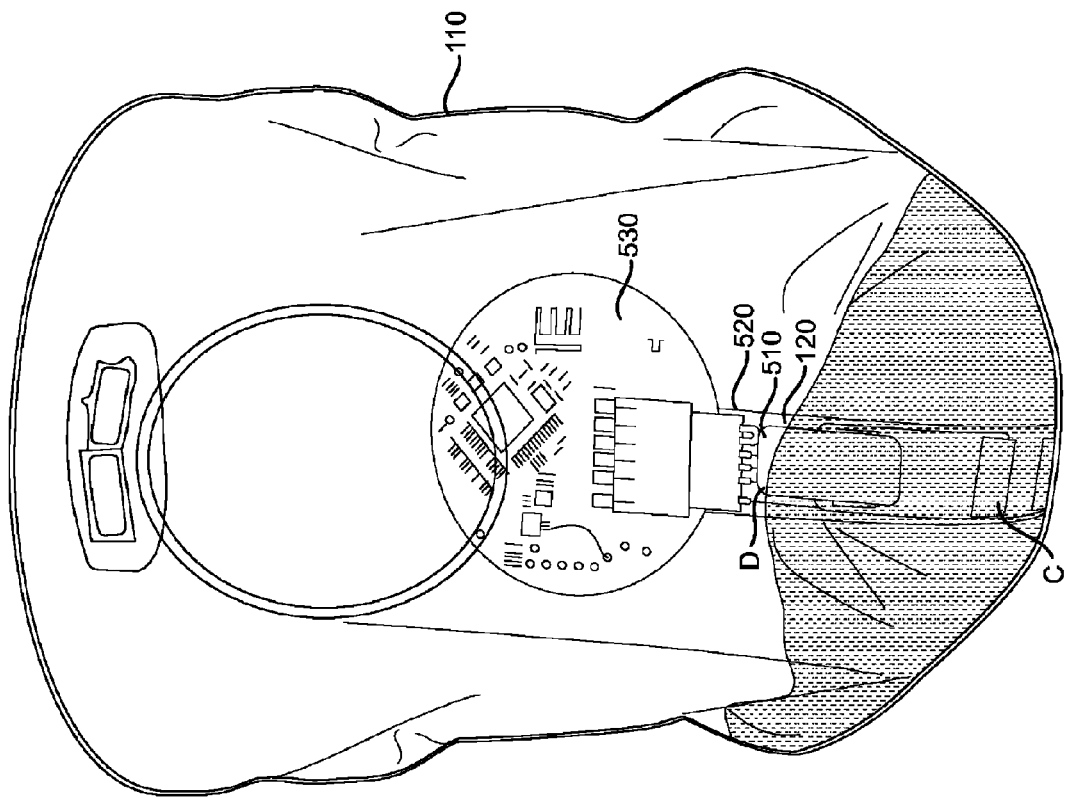

As described earlier, the measurement communicator 530 is configured to transmit stored effluent/fluid measurement data to a mobile device 710. This enables a patient to conveniently access information on the fluid levels in the collection bag. As shown in FIGS. 7A and 7B, a mounting device 520 is attached to a collection bag (for example, an ostomy bag) 110. The mounting device 520 includes a plurality of fluid sensors 510. A measurement communicator 530 is configured to receive and transmit data from the fluid sensors 510.

As shown, four fluid sensors, A, B, C and D are disposed along the length of the mounting device 520. The sensors A-D measure four levels of fluid inside the collection bag 110. When the measurement communicator 530 is powered, it goes into an advertising mode and looks for a suitable mobile device to pair with. A predetermined communication method, for example, Wi-Fi or a Bluetooth Low Energy (BLE) protocol can be used to achieve communication between the measurement communicator 530 and a suitable mobile device 710. The mobile device 710 can be mobile phone or a table PC. The mobile device 710 is configured to receive data notifications from the measurement communicator 530. The mobile device 710 can be configured with or download a customizable dictionary application. In one or more embodiments, the manufacturer of the sensor device 110 can provide the dictionary. The dictionary is used to define the values and read the parameter data transmitted by measurement communicator 530. The measurement communicator 530 can utilize the communication method of the mobile device 710.

After the connection is made, the measurement communicator 530 can start sending data notifications periodically to the mobile device. For example, the measurement communicator 530 can send data notifications every 10 minutes. The data format may be binary. The data can include measurements of one or more parameters, such as, fluid level data (gathered from the fluid sensors) and the X, Y and Z orientation of the patient (gathered from an accelerometer). The data may be transmitted with a predefined delay. For example, the delay may be less than 100 milliseconds. The measurement communicator 530 sends this data out as a notification and controls the frequency of broadcasts.

The mounting device 520 can be characterized by a unique identifier. When the sensor device 120 is connected to the mounting device 520, it reads the identifier and recognizes the mounting device 520. This data is also transmitted to the mobile device 710 with the rest of the data. Each collection bag 110 can be identified uniquely because the mounting device 520 is attached to the collection bag 110. Therefore, when the patient changes the collection bag 110, the change can be easily tracked.

The data transmitted to and saved on the mobile device 710 further includes the time stamp of each measurement. The time stamp serves as a unique identifier for each measurement. The time interval between two measurements is predefined. As such, this time stamp enables the calculation of how many measurements did not reach the mobile device 710.

The measurement communicator 530 can also calculate the rate of filling of the collection bag 110 for each patient. This calculation can be used to extract each patient's pattern of bag filling and therefore make a prediction of when the current bag will be filled up and alert the patient to any abnormalities.

The data saved on the mobile device 710 also includes the measurement of the detected parameter (for example, fluid level in the collection bag and the measurement of the accelerometer).

Figure 7C:
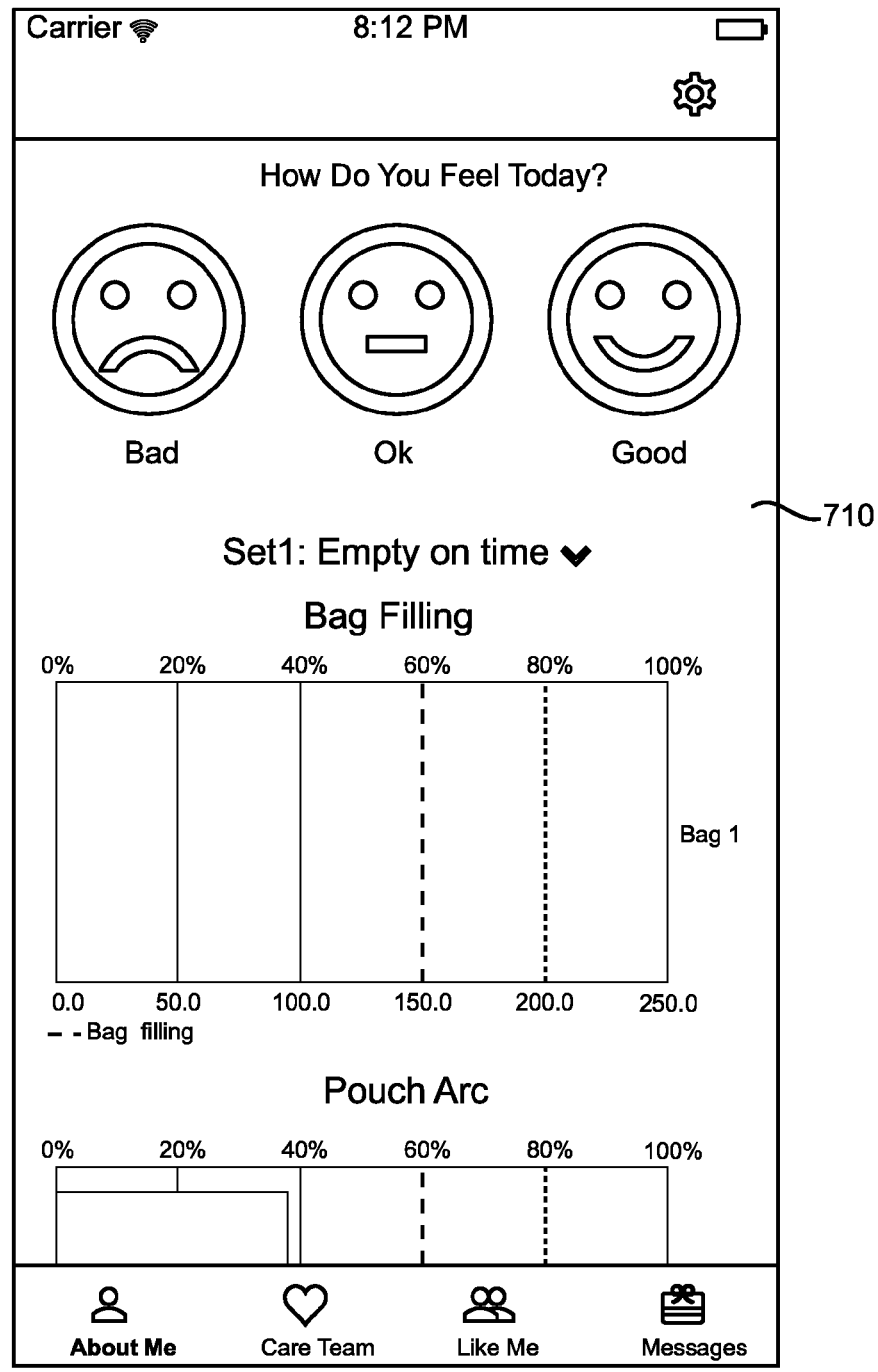
FIG. 7C is an exemplary display screen of a stoma care management software application according to an embodiment.

As shown in FIG. 7C, the measurement of fluid levels can be visually represented on the mobile device 710. The measurement can be dynamically refreshed whenever there is a change in fluid levels. The fluid level visual representation provides the patient with an instant feedback mechanism about his bag filling. The fill rate can also be shown along with an estimate of when the bag needs to be changed.

As shown in FIGS. 7A and 7B, a value can be sent from the measurement communicator 530 to the mobile device 710 to indicate the fill level of the collection bag 110. For example, as shown in FIG. 7A, since the collection bag 110 is empty a corresponding code in binary format is transmitted to the mobile device 710. As shown in FIG. 7A, the mobile device 710 can display a message that none of the sensors are covered, that is, the bag 110 is substantially empty. FIG. 7B shows the fluid level covering all the sensors. As such, a corresponding code is transmitted to the mobile device 710. The mobile device 710 can display a corresponding message that states that all sensors are covered.

After the measurement is received by the mobile device 710, it is read in hexadecimal format and compared against the values provided in the dictionary to determine that the collection bag 710 is empty or full.

In another embodiment (not shown), the measurement communicator is configured to receive data from an accelerometer. Using the data, the direction/orientation of the patient's body can be calculated. This facilitates the determination of whether the patient is lying down, sitting up with his body in an upright position, is leaning forward or any other direction. This information can be used to evaluate the fluid level measurements. For example, if there is a sudden rise in fluid level, the accelerator's measurements can be used to identify the reason for the same. If the accelerometer's measurements indicate that the increased fluid level occurred when the patient was leaning forward, an alert may not be raised. Otherwise, if the accelerometer's measurement indicates that the patient had his body in a straight or upright position, then the interpretation is that a medical reason may have caused the sudden rise in fluid levels. This results in an alert being transmitted to the mobile device to inform the patient of his condition. After sending the data packet, the measurement communicator 530 goes into a deep sleep mode for a set time period to conserve battery power.

Method for Providing Comprehensive Care

Figure 11:
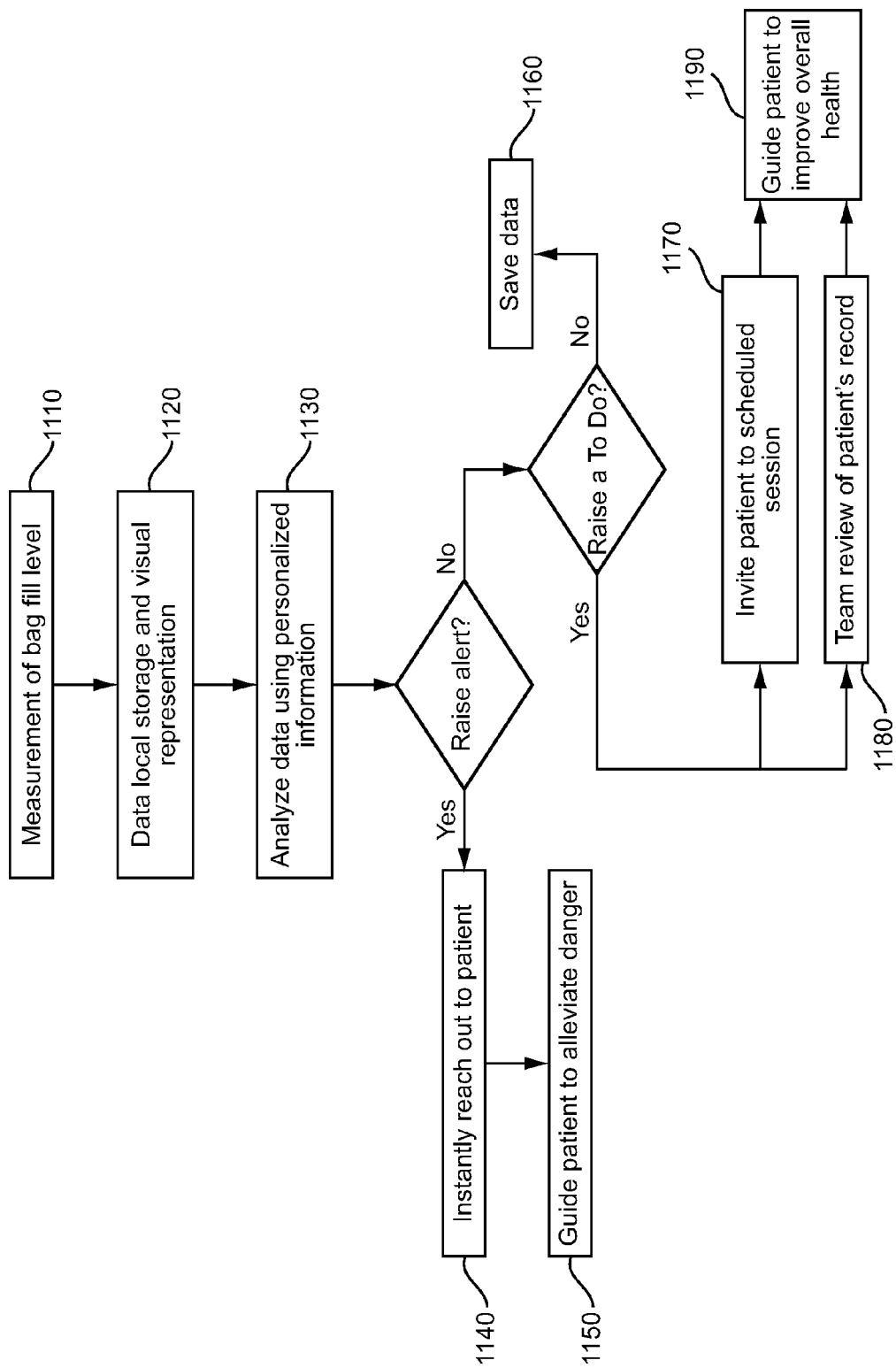
FIG. 11 is an illustration of a method for providing care to a stoma patient according to an embodiment.

An exemplary embodiment for a method of providing comprehensive care to a stoma patient is illustrated in FIG. 11. As shown, the method involves measuring the effluent (or any other parameter) levels in a collection bag to determine bag fill levels 1110. The fill levels can be measured at predetermined time intervals. For example, the fill levels can be measured every 250 milliseconds. an exemplary embodiment, effluent levels may be measured to determine 0%, 25%, 50%, 75% and 100% fill information. The measurements can be communicated to a mobile device using a wireless communication method.

As described earlier, the mobile device may be provided with an application that includes a dictionary to convert the transmitted measurement into hexadecimal values. These values are compared against the values provided in the dictionary to determine fill levels of the bag. The application further provides a visual representation of one or more parameters 1120. The visual representation may include color coded information, graphs, charts or icons on the level measurements, rate of filling up, number of bag changes and number of bags emptied and reused. The visual representation of the measured parameters allows the patients to quickly and easily decipher fill levels.

The measurements are transmitted to a knowledge module where they are analyzed in real-time 1130. The measurements are compared with the patient's records stored in a database. If the measurements are equal to or greater than a predetermined critical value, an alert is raised 1140. An alert is typically raised when the patient is suffering from a potentially life-threatening condition. Any alert mechanism known in the art can be used to notify the patient. For example, a text message can be sent to the user to contact a caregiver. The patient can then be guided to alleviate the potentially dangerous symptoms that caused the discrepancy in the measurements 1150. Even if the measurements do not warrant the raising of an alert, they may be analyzed to determine whether they raise a "To Do" or warning signal. A warning signal may be raised if the measurements are not equal to or greater than predetermined critical value but are within a predefined warning threshold. If a warning signal is also not warranted, the measurements are saved to the patient profile for future reference 1160. However, if a warning signal is raised, the patient may be invited to schedule a session with his Sherpa or caregiver 1170 and then guided to improve his overall health by making required adjustments to their diet, exercise, posture, etc. 1190. Alternately, a team of experts reviews the patient's records 1180 and guides the patient to improve his overall health 1190.

According to another embodiment, a method for determining the effect of diet, medication and activity on the bag fill rate is disclosed. This involves creating a plot of fill rate of the collection bag over a specified period. This further involves: (i) determining how increases or decreases in the certain foods (vegetables, meats, dairy, fish or seafood, fruits, etc.) correlate with increases or decreases in fill rate; (ii) correlating increases or decreases in fluids, including water, fruit juice, carbonated beverages, alcohol, and caffeine, with fill rate; (iii) determining if any particular combinations of foods or fluids cause increases or decreases in fill rate; (iv) correlating use of medications or supplements with fill rate; and (v) determining how increases or decreases in activity correlate with increases or decreases in fill rate. In one embodiment, the individual BMR and BMI may be determined to find the bag fill rates and to compile a set of warning messages to be transmitted to the patient. After the results are tabulated, a patient is provided with education and information, in real time, on managing their diet, medication and activity levels.

Because each individual's unique diet, activity level and physiology (including Body Mass Index and Basal Metabolic Rate) can affect the fill rate and fill levels, a further preferred embodiment involves compiling, at the user portal, the user diet, activity and fill rate information over time, and then establishing projected individual fill rates based on such information (and other known personal information such as BMI and BMR). The projected fill rate is continuously updated over time as data is accumulated. The updating is needed as the projected fill rate is expected to change over time with a user's changing physiology. As a database of projected individual fill rates grows, it allows a more accurate prediction of fill rates for new patients, for whom there is no prior fill rate information. Thus, increased reliability of projected fill rates for new patients is a significant benefit of one preferred embodiment.

In another aspect, the invention relates to uniquely tailored advice and recommendations, particular on diet, based on patient preferences. The advice and recommendations are continually updated and further refined as new information on preferences is added by the user. The individual tailoring of recommendations and advice is performed in view of the user's preferences, limitations and individualized risk assessment as continually updated.

The system may include algorithms that can sort through patient preferences for diet and exercise to provide uniquely tailored advice, recommendations and education for the patient. The number of selections by the algorithm quickly increases as the patient continues to provide feedback, leaving a set of instructions which is so detailed as to essentially be a unique code for the patient.

In one or more embodiments, the method involves progressively personalizing the system for each user using a Progressive User Personalization, or PUP, process. Because no two individuals are alike, the Progressive User Personalization, or PUP, can customize the knowledge module to meet the requirements of each individual user. PUP starts with the individual (not the group) and creates a personalized experience for the user, an experience that continually builds on experiential use of the system and input into the database. Profiles are created, risks are stratified, program results are tracked and measured, interventions are designed based on the experience, and the individual's database become more personalized and tailored to fit their needs and lifestyle delivering content, tips, messages, and relevant information to exploit the "teachable moment" to lead to long-lasting behavior change. The programs are not static but are interactive and expressly tailored to an individual's needs. PUP feeds back rich content to engage individuals to manage their own health, and provides the connectivity and coordination that individuals need to navigate within healthcare system. The technology combines the key elements of simplicity, accessibility and convenience, engagement and community, and tracking and measuring to effect meaningful interventions. PUP is embedded into the program to provide constant virtual health and wellness coaches.

The detailed description presented above is discussed in part in terms of procedures which may be executed on a computer, a network or a cluster of computers. These procedural descriptions and representations are used by those skilled in the art to most effectively convey the substance of their work to others skilled in the art. They may be implemented in hardware or software, or a combination of the two.

A procedure is here, and generally, conceived to be a sequence of steps leading to a desired result. These steps are those requiring physical manipulations of physical quantities. Usually, though not necessarily, these quantities take the form of electrical or magnetic signals capable of being stored, transferred, combined, compared, and otherwise manipulated. It proves convenient at times, principally for reasons of common usage, to refer to these signals as bits, values, elements, symbols, characters, terms, numbers, objects, attributes or the like. It should be noted, however, that all of these and similar terms are to be associated with the appropriate physical quantities and are merely convenient labels applied to these quantities.

Further, the manipulations performed are often referred to in terms, such as adding or comparing, which are commonly associated with mental operations performed by a human operator. No such capability of a human operator is necessary, or desirable in most cases, in any of the operations described herein which form part of the present invention; various operations described herein may be automatic machine operations. Useful machines for performing the operations of the present invention include general purpose digital computers or similar devices.

Selected steps of the method may be executed on a general computer, such as a mainframe computer, personal computer or the like and pursuant to one or more, or a part of one or more, program modules or objects generated from any programming language, such as C++, Java, Fortran or the like. And still further, a step, or a file or object or the like implementing a step, may be executed by special purpose hardware or a circuit module designed for that purpose.

Aspects of the invention are implemented (in one example) in a high level procedural or object-oriented programming language to communicate with a computer. However, the inventive aspects can be implemented in assembly or machine language, if desired. In any case, the language may be a compiled or interpreted language.

The invention may be implemented as a mechanism or a computer program product comprising a recording medium. Such a mechanism or computer program product may include, but is not limited to CD-ROMs, diskettes, tapes, hard drives, computer RAM or ROM and/or the electronic, magnetic, optical, biological or other similar embodiment of the program. Indeed, the mechanism or computer program product may include any solid or fluid transmission medium, magnetic or optical, or the like, for storing or transmitting signals readable by a machine for controlling the operation of a general or special purpose programmable computer according to the method of the invention.

The procedures presented herein are not inherently related to a particular computing environment. The required structure for a variety of these systems will appear from the description given. Again, the capabilities of one or more aspects of the present invention can be implemented in software, firmware, hardware or some combination thereof.

One or more aspects of the present invention can be included in an article of manufacture (e.g., one or more computer program products) having, for instance, computer usable media. The media has therein, for instance, computer readable program code means or logic (e.g., instructions, code, commands, etc.) to provide and facilitate the capabilities of the present invention. The article of manufacture can be included as a part of a computer system or sold separately.

Additionally, at least one program storage device readable by a machine embodying at least one program of instructions executable by the machine to perform the capabilities of the present invention can be provided.

The flow diagram depicted herein is just an example. There may be many variations to the diagram or the steps (or operations) described therein without departing from the spirit of the invention. For instance, the steps may be performed in a differing order, or steps may be added, deleted or modified. All of these variations are considered a part of the claimed invention.

The specific systems and methods described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. The invention has been described broadly and generically herein.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An ostomy bag having:
   a) an attachment site that provides a fluid connection between an interior of the ostomy bag and a patient stoma;
   b) a sensor device having a mounting device that is attached to the ostomy bag via an attachment strip, wherein the mounting device comprising an array of multiple types of parameter sensors, wherein the array of multiple types of parameter sensors are configured to measure different parameters of a stoma effluent received in the ostomy bag, wherein the parameter sensors comprise level measuring sensors placed at different, defined, vertical locations on the bag, the level measuring sensors configured to measure the liquid and solid level of the bag as it fills; and
   c) at least one measurement communicator attached to the ostomy bag, wherein the at least one measurement communicator has an upper end cap and a lower end cap that are fitted together to enclose a data processor, wherein the data processor is configured to: (i) receive a raw measurement signal from a parameter sensor from the array of multiple types of parameter sensors, (ii) reformat the raw measurement signal, (iii) add an identifier corresponding to the time of measurement and an identity of the specific parameter sensor that took the measurement, and to (iv) communicate the reformatted measurement signal along with the identifier to a stoma care management application.

2. The ostomy bag according to claim 1, wherein the array of multiple types of parameter sensors are in communication with the at least one measurement communicator attached horizontally across one section of the bag as shown in FIG. 6A, or it can be attached vertically or diagonally to the bag.

3. The ostomy bag according to claim 2, wherein the array of multiple types of parameter sensors are configured to take measurements at set timed intervals.

4. The ostomy bag according to claim 1, wherein the array of multiple types of parameter sensors measures a percentage of an interior volume of the ostomy bag filled, a volume of bag contents, a temperature of the bag contents, or a liquid flow into the bag.

5. The ostomy bag according to claim 1, wherein the array of multiple types of parameter sensors and the at least one measurement communicator are removably mounted on an exterior of the ostomy bag.

6. The ostomy bag according to claim 1, wherein the array of multiple types of parameter sensors is embedded in the ostomy bag or embedded between an outside elastomeric layer and an exterior surface of the ostomy bag and wherein the at least one measurement communicator is removably mounted on an exterior of the ostomy bag.

7. The ostomy bag according to claim 1, wherein the array of multiple types of parameter sensors communicates with the at least one measurement communicator via a communication conduit.

8. The ostomy bag according to claim 1, wherein the array of multiple types of parameter sensors includes an olfaction sensor or a leakage sensor positioned proximal the attachment site.

9. The ostomy bag according to claim 1, wherein the data processor communicates with a display device and an interactive platform containing patient related data of an ostomy patient.

10. The ostomy bag according to claim 9, wherein at least one parameter sensor includes a liquid flow sensor, wherein the liquid flow sensor communicates with the interactive platform to track stoma effluent flow into and out of the ostomy bag.

11. The ostomy bag according to claim 9, wherein at least one parameter sensor includes an activity sensor, and wherein the activity sensor communicates with the interactive platform to communicate body orientation/direction of the ostomy patient.

12. The ostomy bag according to claim 9, wherein the interactive platform contains a knowledge module configured to analyze data received from the stoma care management application and deliver the analyzed data to the ostomy patient.

13. The ostomy bag according to claim 1, wherein the attachment site is sealingly attached to the patient stoma.

14. An ostomy bag system comprising:
   (a) an ostomy bag having an attachment site that provides a fluid connection between an interior of the ostomy bag and a stoma patient;
   (b) a sensor device attached to an outside surface of the ostomy bag or embedded embedded between an outside elastomeric layer and an exterior surface of the ostomy bag, wherein the sensor device comprises an array of multiple types of parameter sensors comprising level measuring sensors placed at different, defined, vertical locations on the bag, the level measuring sensors configured to measure the liquid and solid level of the bag as it fills;
   c) at least one measurement communicator embedded inside the ostomy bag or embedded between an outside elastomeric layer and an exterior surface of the ostomy bag, wherein the at least one measurement communicator has a data processor, wherein the data processor is configured to: (i) receive a raw measurement signal from a parameter sensor from the array of multiple types of parameter sensors, (ii) reformat the raw measurement signal, (iii) add an identifier corresponding to the time of measurement and an identity of the specific parameter sensor that took the measurement, and to (iv) communicate the reformatted measurement signal along with the identifier to a stoma care management application.

15. The ostomy bag system according to claim 14, wherein the data processor communicates with a display device and an interactive platform containing patient related data of an ostomy patient.

16. The ostomy bag system according to claim 15, wherein at least one parameter sensor includes a liquid flow sensor, wherein the liquid flow sensor communicates with the interactive platform to track stoma effluent flow into and out of the ostomy bag.

17. The ostomy bag system according to claim 15, wherein the at least one parameter sensor includes an activity sensor, and wherein the activity sensor communicates with the interactive platform to communicate body orientation/direction of the ostomy patient.

18. The ostomy bag system according to claim 15, wherein the interactive platform contains a knowledge module configured to analyze data received from the stoma care management application and deliver the analyzed data to the ostomy patient.

* * * * *